United States Patent
Huang

(10) Patent No.: US 6,946,010 B2
(45) Date of Patent: Sep. 20, 2005

(54) METHOD FOR MAKING ABRASIVE COMPOSITIONS AND PRODUCTS THEREOF

(75) Inventor: Yung-Hui Huang, Bel Air, MD (US)

(73) Assignee: J.M. Huber Corporation, Edison, NJ (US)

( * ) Notice: Subject to any disclaimer, the term of this patent is extended or adjusted under 35 U.S.C. 154(b) by 0 days.

(21) Appl. No.: 10/955,252

(22) Filed: Sep. 30, 2004

(65) Prior Publication Data

US 2005/0076582 A1 Apr. 14, 2005

Related U.S. Application Data

(63) Continuation of application No. 10/137,403, filed on May 3, 2002, now Pat. No. 6,860,913, which is a continuation-in-part of application No. 09/641,633, filed on Aug. 18, 2000, now Pat. No. 6,652,611.

(51) Int. Cl.[7] .............................................. B24D 18/00
(52) U.S. Cl. .......................... 51/307; 51/308; 51/309; 51/293; 106/3; 106/35; 423/335; 423/338; 423/339
(58) Field of Search .......................... 51/307, 308, 309, 51/293; 106/3, 35; 423/335, 338, 339; 424/49, 52, 57

(56) References Cited

U.S. PATENT DOCUMENTS

| 4,098,878 | A | * | 7/1978 | Baines et al. | 424/52 |
| 4,343,786 | A | * | 8/1982 | Baines et al. | 424/52 |
| 4,721,615 | A | * | 1/1988 | Griffith et al. | 424/57 |
| 6,403,059 | B1 | * | 6/2002 | Martin et al. | 424/49 |
| 6,419,174 | B1 | * | 7/2002 | McGill et al. | 423/335 |
| 6,652,611 | B1 | * | 11/2003 | Huang et al. | 51/307 |

* cited by examiner

*Primary Examiner*—Michael Marcheschi
(74) *Attorney, Agent, or Firm*—Carlos Nieves; William Parks

(57) ABSTRACT

Method of making abrasive compositions comprised of water-insoluble abrasive polishing agents suspended in an aqueous medium in combination, which avoids the need and associated cost of dry milling the abrasive particle content, and products thereof. In particular, the abrasive compositions made by the method contain appropriately sized abrasive particles provided without the need for drying or dry milling, while also providing an abrasive composition which is Theologically stable, settling-resistant, and re-agglomeration resistant, even during and after transport and/or storage before end-use, such as incorporation into dentifrice formulations or other oral cleaning compositions.

10 Claims, 1 Drawing Sheet

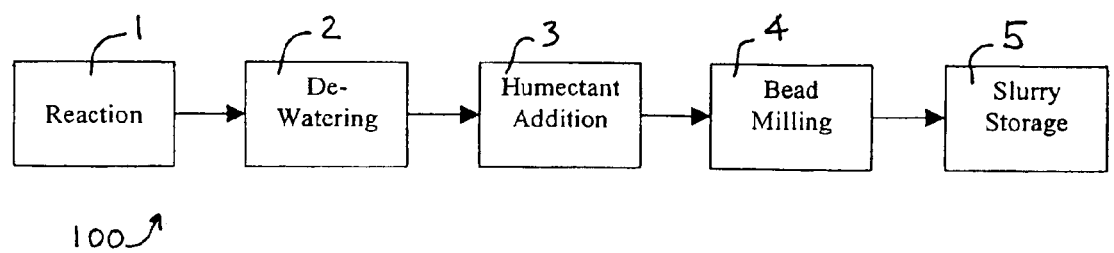

METHOD FOR MAKING ABRASIVE COMPOSITIONS AND PRODUCTS THEREOF

CROSS-REFERENCE TO RELATED APPLICATIONS

This is a continuation of pending U.S. application Ser. No. 10/137,403, filed May 3, 2002, now U.S. Pat. No. 6,860,913, which is a continuation-in-part of U.S. application Ser. No. 09/641,633, filed Aug. 18, 2000, now U.S. Pat. No. 6,652,611, the content of which is incorporated herein by reference in its entirety for all purposes.

BACKGROUND OF THE INVENTION

1. Field of the Invention

This invention relates to a method of making abrasive compositions, and more particularly, it relates to a method of making abrasive compositions comprised of aqueous suspensions of water-insoluble abrasive polishing agents and humectant, with post-reactor dewatering and sizing of the abrasive particles being performed directly via hydraulic chamber press filtering combined with vacuum dewatering, followed by wet comminution, and this invention also relates-to products of this process scheme.

2. Description of the Related Art

An abrasive substance has been included in conventional dentifrice compositions in order to remove various deposits, including pellicle film, from the surface of teeth. Pellicle film is tightly adherent and often contains brown or yellow pigments, which impart an unsightly appearance to the teeth. While cleaning is important, the abrasive should not be so aggressive so as to damage the teeth. Ideally, an effective dentifrice abrasive material maximizes pellicle film removal while causing minimal abrasion and damage to the hard tooth tissues. Consequently, among other things, the performance of the dentifrice is highly sensitive to the abrasive polishing agent ingredient. Conventionally, the abrasive polishing material has been introduced in flowable dry powder form to dentifrice compositions, or via re-dispersions of flowable dry powder forms of the polishing agent prepared before or at the time of formulating the dentifrice.

A number of water insoluble, abrasive polishing agents have been used or described for dentifrice compositions. These abrasive polishing agents include natural and synthetic abrasive particulate materials. The generally known synthetic abrasive polishing agents include amorphous precipitated silicas, silica gels, dicalcium phosphate and its dihydrate forms, calcium pyrophosphate and precipitated calcium carbonate (PCC). Other abrasive polishing agents for dentifrices have included chalk, magnesium carbonate, zirconium silicate, potassium metaphosphate, magnesium orthophosphate, tricalcium phosphate, and the like.

Synthetically-produced precipitated silicas, in particular, have been used as abrasive components in dentifrice formulations due to their cleaning ability, relative safeness, and compatibility with typical dentifrice ingredients, such as humectants, thickening agents, flavoring agents, anti-caries agents, and so forth. As known, synthetic precipitated silicas generally are produced by the de-stabilization and precipitation of amorphous silica from soluble alkaline silicate by the addition of a mineral acid and/or acid gases under conditions in which primary particles initially formed tend to associate with each other to form a plurality of agglomerates (i.e., discrete clusters of primary particles), but without aggregation into a three-dimensional gel structure. The resulting precipitate is separated from the aqueous fraction of the reaction mixture by filtering, washing, and drying procedures, and then the dried product is mechanically comminuted in order to provide a suitable particle size.

The silica drying procedures are conventionally accomplished using spray drying, nozzle drying (e.g., tower or fountain), flash drying, rotary wheel drying, oven/fluid bed drying, and the like, which often require considerable expenditures for equipment and operating costs. A similar issue is associated with other synthetically derived polishing agents, such as silica gel and PCC.

Additionally, conventional abrasive polishing agents intended for dentifrices have required comminution in order to reduce the particle size of the dried precipitated silica product down to a size that does not feel gritty in the mouth of a dentifrice user, while, on the other hand, not being so small as to lack sufficient polishing action. That is, in conventional practice, the median particle size of the silica in the reactor formed by acidulation of a metal silicate is too large for dentifrice applications and the like. To comminute dry silica particulates, grinding and milling equipment have been used, such as a hammer or a pendulum mill used in one or multiple passes, and fine grinding has been performed, for example, by fluid energy or air-jet mill. These additional dry comminution operations entail added cost and process time.

U.S. Pat. No. 3,506,757 to Salzmann describes liquid dentifrices comprising particulate abrasive materials, stably suspended in an aqueous liquid vehicle with the aid of a polysaccharide gum as suspending agent. Similarly, PCT published application no. WO 97/46485 describes silica having a median particle size generally around 12 to 30 $\mu$m provided in the form of a suspension, which can be stabilized using a hydrocolloid, particularly naming polysaccharides such as xanthan gum, guar gum, and water-soluble cellulose ethers. U.S. Pat. No. 5,310,543 describes liquid dentifrices containing particulate siliceous abrasive cleaning agents stably suspended in a liquid medium with the aid of a polysaccharide gum and using a liquid medium specified as being substantially free from polyol-type humectants in order to obtain satisfactory rheological properties.

Among other things, rheologically stable liquid abrasive compositions containing appropriately sized abrasive particles would be desirable that could be prepared without the need for costly drying and dry milling/comminuting post-treatments.

SUMMARY OF THE INVENTION

The above and other objectives, advantages and benefits are achieved by the present invention directed to a method of making abrasive compositions comprised of aqueous suspensions of water-insoluble abrasive polishing agents in combination with humectant, with water content reduction and abrasive particle comminution effected during post-reactor processing under wet conditions.

In one aspect, the invention is directed to a method for preparing an abrasive composition, comprising the steps of introducing, into a reactor container, reaction mixture contents comprising alkali silicate and acid with inter-mixing thereof to form a suspension of precipitated silica; partially dewatering the reaction mixture after forming the precipitated silica by feeding the suspension into a chamber filter press in which the suspension is initially filtered in a plurality of chamber filter plates which provide first filter cake material; further dewatering the first filter cake under reduced pressure in the interior of the chamber filter with heating to provide second filter cake material having a solids content of 40 to 90% by weight; dispersing the silica dewatered mass with humectant; and wet grinding the precipitated silica of the second filter cake material to achieve a desired median abrasive particle size, in which these steps are conducted without any intervening step(s) of dry milling or drying being performed on the precipitated silica which decreases the water content below 5 wt. % at any time.

In a preferred aspect, the method according to this invention is manipulated in manners described herein effective that the precipitated silica particles in the product compositions have a median particle size of about 1 micron to about 30 micron, more preferably about 3 micron to about 15 micron.

This method according to the invention is performed without any intervening dehydration of the abrasive particles into a flowable dry particle mass, or which otherwise would reduce the water content of the filter cake below 5 wt % and more preferably not below about 10 wt % before performing the aforementioned wet grinding procedure on the cake.

Preferably, the wet grinding used in the above-mentioned various embodiments of the invention is accomplished by wet media milling, either as a single stage or multi-stage procedure.

Using this invention, the water-insoluble abrasive particulate product of a silica acidulation reaction can be modified to have the requisite particle size suited for oral cleaning compositions to eliminate the need for drying and comminuting dry silica solids. While not desiring to be bound to any particular theory at this time, it is postulated that the rheological properties of the abrasive compositions prepared by this invention are superior, at least in part, due the avoidance of agglomeration of particles otherwise incurred by the silica particles during conventional silica particle drying procedures. "Drying" of the silica particles, for purposes herein, means silica particles have been dehydrated to an extent that a generally dry flowable powder results as the water content is reduced below about 10 wt %. Thus, "dried" or "dry" abrasive particles have been subjected to such drying, as defined above. By contrast, the abrasive composition products made by the inventive method contain undried silica particles that retain or essentially retain the original structure and chemistry of the reactor silica since they are fluidized and sized in a manner according to this invention that circumvents the need to dry the abrasive particles into a flowable dry state for that purpose.

Moreover, the method of the invention can be practiced more economically because the time as well as the equipment and operating costs otherwise required for extreme particle drying procedures are eliminated. Additionally, the resulting abrasive compositions made by the inventive method are theologically stable, settling-resistant, and re-agglomeration resistant, even during and after transport and/or storage before end-use. The abrasive compositions made by the inventive method are ready-to-use additives for the preparation of oral cleaning compositions, such as dentifrices, toothpastes, and the like, particularly suited as a raw material in a continuous toothpaste making process.

BRIEF DESCRIPTION OF THE DRAWING

The sole FIGURE is a process flow chart of a preferred method scheme for producing an abrasive particle suspension according to the invention.

DETAILED DESCRIPTION OF THE PREFERRED EMBODIMENT(S)

The abrasive compositions made by the method of the present invention are highly stable, portable, storable, ready-to-use aqueous abrasive suspensions and slurries that can be readily formulated on demand with other ingredients to prepare oral cleaning compositions having a high cleaning efficacy without causing undue abrasion on tooth tissues. The essential as well as optional steps of the inventive method are described in more detail below.

Referring to the sole FIGURE, a generalized processing scheme 100 is illustrated for making a silica suspension or slurry according to a preferred embodiment of the invention. The process 100 includes a reaction step (1); a dewatering step (2); a humectant addition step (3); a wet bead milling step (4); and an abrasive particle suspension (slurry) storage step (5), which are discussed in greater detail below.

In the first step of the processing scheme 100, an acidulation reaction 1 is performed to precipitate silica. The initial acidulation reaction is performed in a reaction system equipped with suitable heating equipment. In general, the precipitated silicas made in step 1 may be prepared by a fresh water, or electrolyte solution, acidulation process wherein silica is precipitated by reaction of an alkali metal silicate and a mineral acid in aqueous solution. In the fresh water process, no electrolyte such as alum, $Na_2SO_4$, or NaCl, is present during the acidulation reaction.

A portion of the sodium silicate solution is charged to a reactor container or chamber including agitator means to provide agitation to the container contents.

Preferably, about 0% to 30% of the total stoichiometric amount of sodium silicate solution is placed in the reactor container to serve as initiating nuclei for the silica. The aqueous solution of sodium silicate in the container is then preheated to a temperature in the range of about 60 to 100° C., more preferably about 80 to 95° C. Prior to introduction into the reactor container, the remaining sodium silicate is preferably preheated to about 70 to 95° C. An acid solution is preferably preheated to about 30 to 35° C.

Although sodium silicate is illustrated, it will be understood that any suitable alkali metal silicate could be used. The term "alkali metal silicate" includes all the conventional forms of alkali silicates, as for example, metal silicates, disilicates and the like. Water soluble potassium silicates and sodium silicates are particularly advantageous with the latter being preferred. It should be taken into consideration that the mole ratio of the alkali silicate, i.e., the ratio of silica to alkali metal oxide, contributes, depending on other reaction parameters, to the average pore size of the silica products. In general, acceptable silica products of this invention can be made with silicate molar ratios ($SiO_2:Na_2O$) ranging from about 1.0 to 3.5 and preferably from about 2.4 to about 3.4. The alkali silicate solution supplied to the reactor vessel during various processing steps in the inventive method, as described elsewhere herein, generally can contain between about 8 to 35%, and more preferably between about 8.0% and 15.0%, by weight alkali metal silicate based on the total weight of the alkali metal silicate solution. In order to reduce the alkali silicate concentration of a source solution of alkali silicate to the above-indicated desired range, dilution water can be added to a source solution of alkali silicate before the silicate solution is fed into the reactor, or, alternatively, the dilution water can be combined in situ with the source solution of alkali silicate in the reactor used in the acidulation reaction step 1 with agitation-mixing to formulate the desired concentration of silicate in the alkali metal silicate solution.

The acid, or acidulating agent, can be a Lewis acid or Bronsted acid, and preferably is a strong mineral acid such as sulfuric acid, hydrochloric acid, nitric acid, phosphoric acid, and so forth, and more preferably sulfuric acid, added as a dilute solution thereof (e.g., at a concentration of between about 6 to 35 wt %, more typically about 9.0 to 15.0 wt %).

Once the reactor solution and remaining reactants have reached the desired temperatures, simultaneous addition of the remaining sodium silicate solution and acid into the reactor is commenced. The sodium silicate solution and acid are metered into the reactor over an addition time of about 30 to 90 minutes. Rates of addition of the reactants depend upon the mole ratio, addition time and concentration of the silicate and the concentration of the acid. Generally, 2 moles sodium is neutralized with one mole sulfuric acid.

At the end of this co-addition period, most of the silica has precipitated and the sodium silicate addition is stopped. Addition of the acid is continued until the reactor slurry reaches the desired pH. Once the slurry pH reaches about 7.0, it is preferable to reduce the acid flow rate until the slurry pH approaches the target pH, at which point the acid flow can be stopped and manual adjustment used to reach the target slurry pH. The preferred slurry pH is approximately 4.0 to 7.0, and more preferably between 4.5 to 5.5. At this juncture, the silica has precipitated to provide a mixture of the precipitated silica and the reaction liquor. Once the desired slurry pH is reached, digestion begins and the reaction temperature is raised to approximately 85–99° C., and preferably 91 to 97° C., and digestion is continued at the elevated temperature for approximately 5 to 60 minutes, and preferably for approximately 10 minutes. Acid is added during the digestion step to the extent necessary to maintain a constant pH.

After the digestion step is completed in the reactor used to implement step 1, and any subsequent pH adjustment conducted, the reaction batch is dropped. Although the above-described general protocol are preferred for synthesizing the precipitated silica to be conditioned according to this invention, it will be appreciated that other grades of precipitated silicas, such as very low to medium structure synthetic silicas in accordance with the definitions set forth in J. Soc. Cosmet. Chem., 29, 497–521 (August 1978), and Pigment Handbook: Volume 1, Properties and Economics, 2nd ed., John Wiley & Sons, 1988, p. 139–159, generally can be used in the practice of this invention.

Referring again to the sole FIGURE, in step 2 of the illustrated process, dewatering is performed on the reaction mass obtained from step 1. In one preferred aspect, so-called "J-Vap" processing, or similar chamber filter press processing, is preferred in the implementation of step 2 of the preferred embodiment of the invention as illustrated in THE SOLE FIGURE.

Non-limiting illustrations of methods and equipment arrangements for conducting such J-Vap processing that can be adapted for use in the practice of the filtering/dewatering step of the present invention can be found, for example, in U.S. Pat. No. 5,558,773 and EP 0 978 304 A2, which descriptions are incorporated herein by reference. Other examples of J-Vap processing equipment include commercially available equipment for this purpose, such as that illustrated in the working examples below. The J-Vap processing equipment employed must permit reliable and accurate control over the level of water removal to meet the criterion set forth herein for that parameter.

The J-Vap processing arrangement generally includes a series of reduction chambers in which the washing and dewatering of the reaction slurry is conducted. The reduction chambers are tightly clamped together in the filter press module. An energy conversion module also is included that supplies heated water for the pressurization of the reduction chambers and also includes a vacuum system used during dewatering performed after an initial pressure filtering stage.

In one exemplary suitable arrangement, the chamber filter press of the J-Vap processing system is selected as including a plurality of alternating diaphragm squeeze plates and filter plates covered by respective liquid-permeable filter membranes, in which the squeeze plates and filter plates define abrasive suspension introduction and flow passages therebetween, wherein the squeeze plates include a diaphragm that is expandable toward an adjoining filter plate effective to increase solid/liquid separation in the abrasive suspension in which liquid is transmitted through the adjoining liquid-permeable membrane, and the filter plates including respective interior filtrate drainage chambers for drainage of liquid filtered from the abrasive suspension.

During an initial filtering stage performed on abrasive slurry supplied from the reactor, the slurry wet cake is washed with water, then air blow down commences to remove surface water from the cake. Thereafter, the diaphragm is expanded by introduction of heated fluid effective to expand the diaphragm and heat the abrasive suspension effective to promote water removal from the filter material. That is, slurry from the reactor is pumped into the reduction chambers where initial filtration occurs and the free liquid is drained away. After the initial filtration stage, vacuum-promoted dewatering is performed. For example, the reduction chambers are pressurized with heated water, and a vacuum is introduced. For example, in a second stage of the dewatering process as performed in the J-Vap processing system, the drainage chambers are connected to a vacuum source effective to remove vaporized portions of the abrasive suspension.

The dewatering time is set to achieve the desired water reduction. After the dewatering stages are completed, the reduction chambers are separated from one another and the dewatered filter cake material is discharged and proceeds to the humectant addition step.

Illustrative, non-limiting conditions for conducting such J-Vap dewatering, when used to perform the dewatering step 2 in the sole FIGURE according to the preferred embodiment of the invention, include the following general conditions:

De-water time: 0 to 6 hours;

Feed Pressure: 20–80 psi (138–552 kPa);

Feed temp: 70–180° F. (21–82° C.);

Hot water temp: 120–180° F. (49–82° C.);

Blow down air pressure: 20–80 psi (138–552 kPa);

System Vacuum: 20–29 in. Hg (68–98 kPa);

Squeeze air pressure: 20–100 psi (138–552 kPa); and

Solids content out of J-Vap: 40–90%.

The humectant mixing of step 3 in the sole FIGURE preferably is achieved under 200–4000 rpm.

The reaction mass is filtered and washed with water to reduce the $Na_2SO_4$ level to less than 5%, and preferably less than 2%, by weight (e.g., 0.5 to 1.5%). The resulting dewatered mass generally contains about 40 to about 90 wt % solids content. The pH of the washed filter cake can be adjusted, if necessary.

Referring now to step 3 in the sole FIGURE, a humectant, of the types described below, must be added with mixing in amounts described herein to refluidize the dewatered mass.

For step 3 in the sole FIGURE, a humectant is added in an amount of about 3 to about 80 wt %, preferably about 5 to about 60 wt %, more preferably about 20 to about 50 wt %, and can be even less than 30 wt % (e.g., 3 to <30 wt %), based on the total slurry weight. The humectant preferably is a polyol, such as glycerin, sorbitol, polyethylene glycol, polypropylene glycol, hydrogenated starch hydrolyzate, xylitol, lactitol, and hydrogenated corn syrup, used singly or as mixtures thereof. Glycerin and sorbitol are preferred, as used individually or in combinations. Glycerin is readily obtainable in 99.5 wt % solutions, while sorbitol is often commercially obtained as a 70 wt % solids aqueous solution.

Functionally, the term humectant is customarily understood to refer to a compound which facilitates and ensures moisture retention by compositions incorporating same so as to prevent drying out of the composition upon its exposure(s) to air. Preferably, the mixing of the humectant and silica is done in a high shear mixer, such as by adding the silica press cake or crumbles into a mixer vessel containing the specified amount of humectant and then mixing. Examples of useful mixers in this regard are a Cowles Model W.24x, high shear mixer, a Motoregler Dispermat CV high shear mixer, or a Hockmeyer Lab 2 type disperser from Hockmeyer Equipment Company. The fluidization using humectant provides an essentially uniform and thorough dispersion and distribution of the silica particles in the liquid medium (carrier), which is highly resistant to settling.

Referring now to the wet bead milling step 4 in the sole FIGURE, comminution is needed because the silica particles in the abrasive suspension drawn from the reactor of step 1 generally have a median particle size (MPS) of greater than about 50 $\mu$m to about 100 $\mu$m, and more typically about 65 $\mu$m to about 85 $\mu$m. These particles sizes are unacceptable for applications such as oral cleaning compositions. Namely, smaller abrasive particles are needed so that the particles are not gritty in texture to a user, yet the particles must be large enough to provide the requisite polishing action on teeth. For oral cleaning compositions, silica particle sizes between about 1 and about 30 $\mu$m are generally required, and a median particle size of between about 3 to 15 $\mu$m is preferred in this invention.

To comminute the abrasive particles (typically agglomerates) in step 4, the slurry received after humectant addition in step 3 is fed to a wet media grinding station. No extraneous organic dispersant is added to the slurry before wet grinding is performed in step 4. Either a single stage wet media mill or a multi-stage wet milling operation in step 4 can be used. For example, the multi-stage wet media grinding station, in one embodiment, can be comprised of two or more separate mills through which the slurry is successively progressed. Alternatively, the multi-stage wet media grinding station can be comprised of a single mill in which the slurry is fed through the single mill in multiple passes using recirculation. The amount of energy dissipated into the feed slurry at each mill stage, or in each pass through a single mill in a multi-pass form of multi-stage milling, generally is kept approximately the same, although this is not necessarily required. Multi-stage wet media milling permits longer residence times to be applied.

The wet media mill types used as the mill or mills described above in the multi-stage grinding station independently can be ball mills, wet vertical media mills, wet horizontal media mills and the like. One preferred type of wet grinding mill used in the practice of this invention is a Model HML 1.5 Premiere Mill manufactured by Lightnin, Inc., Reading, Pa. The Premier mill is a horizontal style media mill. The milling media used preferably are ceramic beads, e.g., zirconium oxide beads, of about 1 to 3 mm in size, which are loaded in the mills at about 20 to 80 vol %.

In one preferred non-limiting illustration, the wet bead mill used to conduct step 4 in the sole FIGURE generally is operated under the following conditions:

Bead loading: 20–60%; and

Bead mill rotor speed: 500–3500 ft/minute (152–1067 m/minute).

In keeping with an objective of this invention of reducing silica particles without the need for drying and dry milling procedures, the total amount of shearing forces applied to the slurry or fluidized press cake during wet grinding should be sufficient to reduce the median particle size (MPS) to between about 1 to about 30 microns ($\mu$m), preferably between about 1 and about 25 microns, and more preferably between about 3 and about 15 microns. The abrasive particles in the wet milled abrasive composition have less than 1.5 wt % fraction of +325 mesh size particles.

The resulting abrasive suspension derived from step 4 generally comprises about 10 to about 60 weight percent of abrasive particles, from about 3 to about 80 weight percent of humectant, and from about 5 to about 50 weight percent water (preferably 5 to 30 wt. % water). For purposes of this invention, the terminology "abrasive particles" encompasses primary particles, aggregates and/or agglomerates, unless indicated otherwise.

The finished abrasive suspension or slurries at step 5 can then be piped, loaded for transport, or stored, until needed for later usage, such in the preparation of dentifrices or other oral cleaning compositions. In this regard, the aqueous suspension of abrasive particles typically will be combined with at least one of additional water, additional humectant as needed, a binder, a fluoride ion-providing compound, a flavoring agent, a coloring agent, a whitening agent, a preservative, an anti-plaque compound, a foaming agent, and an anti-microbial agent.

The abrasive particle suspension obtained at step 5 generally has a viscosity of ranging from about 100 cps to 700,000 cps, as measured at 25° C. measured on a Brookfield RVT Viscometer with a T-F spindle at a speed of 5.0 rpm on a Helipath stand, and a solids settling rate of less than 30 wt % after three weeks storage at about 25° C. The resulting abrasive suspension also possesses excellent viscosity build up property. Namely, the inventive abrasive compositions possess an advantageous viscosity build up property in that it is sufficiently high to reduce requirements for thickeners or binders commonly used in the dentifrice formulations and other related ultimate uses, while not being so high as to adversely impact the useful silica loading levels due to otherwise causing an overly rapid viscosity increase upon addition.

The precipitated silica to be wet milled according to the invention is introduced thereto as a dewatered mass fluidized with humectant, experimentally observed to yield an abrasive slurry or suspension retaining enhanced Theological stability and settling-resistance. Additionally, the wet milled product slurry also does not experience significant re-agglomeration of the silica into larger particle sizes after the wet milling operation. Thus, the abrasive composition provided at this stage of processing is highly stable and particle sized appropriately so as to be portable, storable, and used on demand as a ready-to-use multi-component additive for more complex formulations such as dentifrices and other liquid oral cleaning compositions.

The high settling-resistance of the resulting abrasive compositions also makes it possible to avoid the need before end use for introduction of temporary stabilizers such as inorganic suspending agents (e.g., clays, fumed silicas) or organic binders (e.g., polysaccharides). Preferably, no polysaccharide binder is present in the inventive abrasive composition, or only minuscule amounts at most, viz., less than 0.20 wt % polysaccharide and more preferably less than 0.05 wt % polysaccharide is present, if at all, in the abrasive composition obtained at step 5 (the sole FIGURE). Polysaccharide binders include water-soluble cellulose ethers, guar gum, and xanthan gum, and so forth, and these binder materials are not needed to rheologically stabilize and provide adequate viscosity build up property in the abrasive compositions of the present invention. When the inventive abrasive composition is ultimately combined with other requisite materials, e.g., thickeners, liquid vehicle, fluoride compounds, tartar control agents, and so forth, to form a dentifrice or other oral cleaning composition, it has been observed that the binder then can be combined with the inventive abrasive composition and the other dentifrice ingredients, such as the thickeners and liquid vehicle, without adverse impact on the rheological or silica settling properties.

A preservative, such as an anti-microbial agent (i.e., an anti-bacterial and/or anti-fungal agent), optionally can be added to the dewatered mass during the humectant addition step. The preservative in this regard can be selected, for example, from the group consisting of sodium benzoate, tetrasodium pyrophosphate, propyl-p-hydroxy-benzoate, and methyl-p-hydroxy-benzoate (methyl paraben). Effective amounts of the preservative seen to adequately prevent microbial growth are less than about 0.5 wt % based on the finished toothpaste weight. The preservative, as used in these amounts, does not impact the advantageous rheological properties of the abrasive composition.

An important aspect of this invention is that the aqueous suspension of milled abrasive particles provided at step 5 can be continuously maintained at a total liquid content of at least 5 wt %, preferably at least 20 wt %, up until an additional step of incorporating said aqueous suspension of abrasive particles into a dentifrice composition or other oral cleaning composition without the need to dry the silica or perform dry milling. No drying or dry milling of the precipitated silica need occur from the time the silica is synthesized up until its incorporation into an oral cleaning composition. While not desiring to be bound to any particular theory at this time, it is postulated that drying and dry milling processes impact the surface and chemical properties of the silica particles in unpredictable or even adverse manners. The present invention avoids these impacts of drying and dry milling.

The silicas provided in the above-illustrated abrasive compositions are preferably characterized as synthetic hydrated amorphous silicas, known as silicon dioxides or $SiO_2$.

These precipitated silicas can be characterized as very low to medium structure synthetic silicas.

In addition to the above-described step 1 methodology of precipitating the raw synthetic amorphous silicas in the reactor, the preparation of the raw silica is not necessarily limited thereto and-it also can be generally accomplished in accordance with the methodologies described, for example, in prior U.S. Pat. Nos. 3,893,840, 3,988,162, 4,067,746, 4,340,583, 5,225,177 and 5,891,421, all of which are incorporated herein by reference, as long as such methods are appropriately modified to append the post-processing treatment(s) used in at least steps 2, 3 and 4 of the preferred inventive method, as illustrated in the sole FIGURE and discussed above. As will be appreciated by one skilled in the art, reaction parameters which affect the characteristics of the resultant precipitated silica include: the rate and timing at which the various reactants are added; the levels of concentration of the various reactants; the reaction pH; the reaction temperature; and/or the rate at which any electrolytes are added.

The precipitated silicas derived in the abrasive compositions of this invention generally have the following properties: 10% Brass Einlehner hardness values in the range between 0.5 and 30, linseed oil absorptions between about 40 to about 200 cc/100 g, RDA (Radioactive Dentin Abrasion) values between about 30 to about 200, and PCR (Pellicle Cleaning Ratio) values of 50 to 200.

Although silicas have been illustrated herein as the abrasive polishing agent component provided in the abrasive compositions being produced by this invention, it will be understood that the principles of the present invention are also considered applicable to suspensions or slurries of other water-insoluble abrasive particles that can be synthesized in a reactor without the need for any intervening drying or dry milling steps. Other such water-insoluble particles include, for example, silica gels, dicalcium phosphate or its dihydrate forms, calcium pyrophosphate and precipitated calcium carbonate (PCC).

Examples of use of these optional dentifrice ingredients are described herein and/or, for example, in Reissue Pat. No. 29,634, and U.S. Pat. Nos. 5,676,932, 6,074,629, and 5,658,553, and the patents cited therein, all being incorporated herein by reference. These optional ingredients, if used, can be used at levels that are customarily seen in dentifrice formulations.

The precipitated silica component of the above-described silica suspension product (available at step 5 in the sole FIGURE), when incorporated into dentifrice compositions, is present at a level of from about 10% to about 50% by weight, more preferably from about 10% to about 35% by weight, when the dentifrice is a toothpaste. Overall dentifrice or oral cleaning formulations incorporating the abrasive compositions of this invention conveniently can comprise the following possible ingredients and relative amounts thereof (all amounts in wt %):

| Dentifrice Formulation: | |
| --- | --- |
| Ingredient | Amount |
| Liquid Vehicle: | |
| humectant (s) (total) | 5–70 |
| deionized water | 5–70 |
| binder (s) | 0.5–2.0 |
| anticaries agent | 0.1–2.0 |
| chelating agent (s) | 0.4–10 |
| silica thickener | 3–15 |
| anionic surfactant (s) | 0.5–2.5 |
| abrasive | 10–50 |
| sweetening agent | <1.0 |
| coloring agents | <1.0 |
| flavoring agent | <5.0 |
| preservative | <0.5 |

Useful silica thickeners include, for example, an amorphous precipitated silica such as Zeodent® 165 silica. Other preferred silica thickeners are Zeodent® 163 and Zeofree® 153 silicas, all available from J. M. Huber Corporation, Havre de Grace Md., USA.

EXAMPLES

The following examples are presented to illustrate the invention, but the invention is not to be considered as limited thereto. In the following examples, parts are by weight unless indicated otherwise.

Example 1

A series of batches of precipitated silicas were prepared in a reactor as follows, which thereafter were subjected to certain dewatering, fluidization, and wet milling described below, without any drying or dry milling occurring, to observe the effects of the post-processing procedures that were applied.

Two separate batches of precipitated silica were prepared as follows:

The first batch was prepared by adding 673 gallons (2547 L) of water to a reactor and heated to 88° C. Sodium silicate (13.3%, 2.65 mole ratio of $SiO_2:Na_2O$) was preheated to 85° C. then added to the reactor at a rate of 71.3 gpm (270 L/min). After 53.5 gallons (202 L) of sodium silicate were added to the reactor vessel, sulfuric acid (11.4%) addition was begun at a rate of 36.5 gpm (138 L/min). The simultaneous addition of sodium silicate and sulfuric acid continues for 60 minutes, after which time the sodium silicate addition is discontinued. The acid flow was continued until the batch pH dropped to 5.4, at which time the acid flow was stopped. The batch was then digested at 93° C. for 5 minutes, with the pH adjusted back towards 5.4 as needed throughout digestion. After digestion, the pH was manually adjust to 5.4+/−0.1 pH, and the batch was dropped. The batch was rotary vacuum filtered and washed to less than about 2% sodium sulfate.

The second batch of precipitated silica was prepared by adding 502 gallons (1900 L) of sodium silicate (13.0%, 2.50 mole ratio of $SiO_2:Na_2O$, 85° C.) to a reactor. Simultaneous addition of sodium silicate (13.0%, 2.50 mole ratio of $SiO_2:Na_2O$, 85° C.) at a rate of 102.4 gpm (387.6 L/min) and sulfuric acid (11.4%) at a rate of 45 gpm (170 L/min) was continued for 48 minutes, after which time the sodium silicate addition is discontinued. The acid flow was continued until the batch pH dropped to 5.1.+/−.0.1, at which time the acid flow was discontinued. The batch was then digested at 93° C. for 10 minutes, with the pH adjusted back towards 5.1 as needed throughout digestion. After digestion, the pH was manually adjust to 5.1.+/−.0.1, and the batch was dropped. The batch was rotary vacuum filtered and washed to less than about 2% sodium sulfate.

Batch 1 silica prepared as described above was split into 3 portions and dewatered separately in a J-Vap dewatering system (model JVAP 470/100 available from US Filter Corporation, Holland, Mich.) under the conditions listed in Table I below. Batch 2 was likewise separately dewatered in a J-Vap dewatering system under the conditions listed in Table I. Specifically, the silica wet cake at about 35% solids was agitated and heated to the desired feed temperature, then was pumped into the J-Vap system. Blow down (BD) air was initiated and continued for 10 minutes for batch 1 and 15 minutes for batch 2. Immediately thereafter pressure squeeze (SQZ) was initiated and held for the duration of the dewatering cycle. During the whole dewatering cycle, vacuum was drawn to about 27 inch Hg and hot water (82° C.) was recirculated for the stated "De-water time" to remove excess water from the product. Solids content was measured on the dewatered product by drying the resulting silica crumbles at 150° C. for 16 hours.

TABLE I

| Batch No. | Feed solids % | Feed Temp. ° C. | Feed Pressure (psi) | BD/SQZ Pressure (psi) | BD Time Min. | De-Water Time hr. | Resulting % Solids |
|---|---|---|---|---|---|---|---|
| 1A | 34 | 71 | 40 | 40/30 | 10 | 1 | 73.2 |
| 1B | 34 | 71 | 40 | 40/30 | 10 | 1.5 | 77.2 |
| 1C | 34 | 71 | 40 | 40/30 | 10 | 2 | 83.7 |
| 2 | 35 | 24 | 40 | 60/90 | 15 | 3 | 69.3 |

Batch 2 was split into 2 portions, denoted 2A and 2B, before dispersion. Batch 2A was pH adjusted by adding 98% sulfuric acid to pH 7 and batch 2B was pH adjusted by adding 98% sulfuric acid to pH 6.4. These batches then were each fluidized by mixing the silica "crumbles" obtained from the dewatering process with sorbitol (70%) and water to form compositions of the silica:water:sorbitol ratios listed in Table II below, respectively. All three batch 1 samples were mixed at 1500 rpm and both batch 2 samples were mixed at 2000 rpm. Mixing of the silica crumbles and sorbitol humectant was obtained by using a Cowles disperser Model W24x.

The five silica:water:sorbitol slurries were separately pumped through a horizontal Premier mill, model HML-1.5, having a 1.5 liter grinding chamber loaded with 0.6 liters (40% loading) of 1.8 to 2.2 mm sized zirconia media beads having a specific gravity of 3.7. The bead mill rotor speed, in meters per minute (MPM), and slurry feed rates, in liters per minute (LPM) are given in Table II below.

TABLE II

| | Humectant Dispersion | | Beadmilling | |
|---|---|---|---|---|
| Batch Number | Shear Mixer RPM | Silica:Water:Sorbitol | Rotor Speed MPM | Feed Rate LPM |
| 1A | 1500 | 2:1:2.8 | 945 | 1.0 |
| 1B | 1500 | 2:1:2.7 | 488 | 1.0 |
| 1C | 1500 | 2:1:3.0 | 457 | 1.0 |
| 2A | 2000 | 2:1:1.4 | 762 | 0.5 |
| 2B | 2000 | 2:1:1.4 | 762 | 0.5 |

The results, insofar as the median particle size and oil absorption of the wet milled silica particles in the slurries of respective batches 1A to 2B are summarized in Table III below.

TABLE III

| Batch Number | Oil Absorption ml/100 g | Median Particle Size $\mu$m |
|---|---|---|
| 1A | 100 | 4.44 |
| 1B | 99 | 7.35 |
| 1C | 99 | 8.25 |
| 2A | 82 | 3.77 |
| 2B | 82 | 8.04 |

The silica properties described herein were measured as follows.

The precipitated silicas used in the dentifrice compositions of this invention have a median particle size (MPS) measured using a Microtrac II apparatus, Leeds and Northrup.

Oil absorption, using linseed oil, was determined by the rubout method. This method is based on a principle of mixing oil with silica by rubbing with a spatula on a smooth surface until a stiff putty-like paste is formed. By measuring the quantity of oil required to have a paste mixture which will curl when spread out, one can calculate the oil absorption value of the silica, which is the value which represents the volume of oil required per unit weight of silica to saturate the silica sorptive capacity. For purposes of the oil absorption measurement, the silica sample tested was obtained directly from the silica product of the J-Vap procedure and dried at 105° C. for about 12 hours before testing. Calculation of the oil absorption value was done as follows:

Oil absorption = (ml oil absorbed/weight of silica, in grams) × 100

= ml oil/100 gram silica

Example 2

Toothpaste formulations were prepared using the inventive silica:water:sorbitol slurries of batches 1A, 1B, 1C, 2A and 2B. Comparison toothpaste formulations, referenced as "1D" and "2D" respectively, were prepared with batch 1 and batch 2 silica that had been spray dried and milled for comparison purpose. The spray drying used on the comparison samples involved drying silica to 7.0% $H_2O$, +/−1% using an atomizing spray drying means having an inlet temperature at 480° C. The spray dried samples of the comparative silica were then Hammermilled to 8–14 μm.

Toothpaste formulations were prepared to demonstrate the ready-to-use on demand capabilities of the inventive abrasive slurry compositions. Dentifrices were formulated with a portion of silica slurry 1A, 1B, 1C, 2A and 2B, as described above, and other ingredients, in amounts indicated in grams, as described in Table IV below. For comparison, portions of the dried and milled silica 1D and 2D described above were separately incorporated in toothpaste formulations. Properties of these dentifrice formulations are given in Table V below.

To prepare the dentifrices, the following procedure was followed. Additional humectant (glycerin, sorbitol) for combination with the humectant amount being introduced via the abrasive-humectant suspension to achieve the full amount of humectant needed for the dentifrice, sodium carboxymethylcellulose (CMC-7MXF, from the Aqualon division of Hercules Corporation, Wilmington, Del.), and polyethylene glycol (CARBOWAX 600, from the Union Carbide Corporation, Danbury, Conn.), are mixed together to form a first admixture. The deionized water amount not included in the abrasive-humectant suspension, sodium fluoride, sodium benzoate and sodium saccharin are also mixed together until these ingredients are dissolved to form a second admixture. These two mixtures are combined with stirring. Thereafter, color is optionally added and the combined mixture is stirred with a Lightnin mixer to obtain a "Pre-mix".

The "Pre-mix" is placed in a Ross mixer (Model 130 LDM) and the abrasive-humectant suspension, silica thickener (Zeodent® 165 silica available from J. M. Huber Corporation, Edison, N.J.) and any required $TiO_2$ are added and mixed without vacuum. A 30 inch ($H_2O$) vacuum (7.47 kPA vacuum) is then drawn and the resultant admixture is stirred for approximately 15 minutes. Lastly, sodium lauryl sulfate and flavor are added and the admixture is stirred for approximately 5 minutes at reduced mixing speed.

The resulting dentifrice composition is sealed in toothpaste tubes and held under appropriate conditions for later testing.

TABLE IV

| | Toothpaste No. | | | | | | |
|---|---|---|---|---|---|---|---|
| | 1 | 2 | 3 | 4 | 5 | 6 | 7 |
| Glycerin, 99.5% | 11.000 | 11.000 | 11.000 | 11.000 | 10.000 | 10.000 | 10.000 |
| Sorbitol, 70.0% | 26.000 | 27.000 | 24.000 | 51.107 | 50.607 | 39.127 | 39.127 |
| Deionized Water | 0.00 | 0.00 | 0.00 | 8.000 | 10.000 | 3.420 | 3.420 |
| Carbowax 600 | 3.000 | 3.000 | 3.000 | 3.000 | 3.000 | 3.000 | 3.000 |
| CMC-7MXF | 0.400 | 0.400 | 0.400 | 0.400 | 0.400 | 0.400 | 0.400 |
| Sodium Benzoate | 0.500 | 0.500 | 0.500 | 0.500 | 0.500 | 0.500 | 0.500 |
| Sodium Saccharin | 0.200 | 0.200 | 0.200 | 0.200 | 0.200 | 0.200 | 0.200 |
| Sodium Fluoride | 0.243 | 0.243 | 0.243 | 0.243 | 0.243 | 0.243 | 0.243 |
| Zeodent ® 165 silica thickener | 5.500 | 5.500 | 5.500 | 5.500 | 5.000 | 5.000 | 5.000 |
| 1D silica (control) | 18.000 | — | — | — | — | — | — |
| 1A silica:water:sorbitol slurry | — | 51.107 | — | — | — | — | — |
| 1B silica:water:sorbitol slurry | — | — | 50.107 | — | — | — | — |
| 1C silica:water:sorbitol slurry | — | — | — | 53.107 | — | — | — |
| 2D silica (control) | — | — | — | — | 18.000 | — | — |
| 2A silica:water:sorbitol slurry | — | — | — | — | — | 36.050 | — |
| 2B silica:water:sorbitol slurry | — | — | — | — | — | — | 36.050 |
| FD&C Blue #1, 1.00% Soln. | 0.200 | 0.200 | 0.200 | 0.200 | 0.200 | 0.200 | 0.200 |
| Sodium Lauryl Sulfate | 1.200 | 1.200 | 1.200 | 1.200 | 1.200 | 1.200 | 1.200 |
| Flavor | 0.650 | 0.650 | 0.650 | 0.650 | 0.650 | 0.650 | 0.650 |

The toothpaste properties described herein were measured as follows, unless indicated otherwise.

The toothpaste viscosity is measured utilizing a Brookfield Viscometer Model RVT equipped with a Helipath T-F spindle and set to 5 rpm by measuring the viscosity of the toothpaste at 25° C. at three different levels as the spindle descends through the toothpaste test sample and averaging the results. Brookfield viscosity is expressed in centipoise (cP).

The pH values of the toothpaste mixtures (25 weight % slurry) encountered in the present invention can be monitored by any conventional pH sensitive electrode.

Aesthetic properties of toothpaste (stand-up, separation) were measured visually. About a one inch ribbon of toothpaste was squeezed from a tube onto a piece of ordinary white notebook paper. After waiting 3–5 minutes, aesthetic property observations were recorded.

Stand-up refers to the shape of the toothpaste ribbon and relates to the paste's ability to stay on top of a toothbrush without sinking in-between the bristles. A scale of 1–10 is used, with a stand-up rating of 10 being good and meaning the ribbon retained its shape. A stand-up rating of 1 is poor, meaning the ribbon flattens out, losing its shape.

Separation refers to the toothpaste formulation's integrity. Solid and liquid phases of the toothpaste may separate, usually due to too little binder or thickener. Liquid will be visible around the squeezed ribbon of paste if there is separation. Separation ratings are on a scale of 1–10 with a rating of 10 meaning no separation; a rating of 1 meaning major phase separation; and intermediate ratings meaning that an amount of liquid appears around ribbon.

The Radioactive Dentin Abrasion (RDA) values of the precipitated silica compositions used in this invention are determined according to the method set forth by Hefferen, Journal of Dental Res., July-August 1976, 55 (4), pp. 563–573, and described in Wason U.S. Pat. Nos. 4,340,583, 4,420,312 and 4,421,527, which publications and patents are incorporated herein by reference.

The PCR test is described in "In Vitro Removal of Stain With Dentifrice" G. K. Stookey, et al., J. Dental Res., 61, 1236–9, 1982.

feeding the suspension into a chamber filter press in which the suspension is filtered by a plurality of chamber filter plates to partially dewater the suspension to produce first filter cake material;

dewatering the first filter cake material under reduced pressure in the interior of the chamber filter and with heating to provide second filter cake material having a solids content of 40 to 90% by weight;

fluidizing the abrasive particles in the second filter cake material by combining humectant with the abrasive particles with mixing effective to provide an aqueous suspension of abrasive particles; and wet grinding the aqueous suspension of abrasive particles; wherein the chamber filter press includes a plurality of alternating i) filter plates covered by respective liquid-permeable filter membranes, and ii) diaphragm squeeze plates that each include a diaphragm that is expandable toward an adjoining filter plate; wherein the squeeze plates and filter plates define abrasive suspension flow passages being the areas between each diaphragm included with a squeeze plate and each liquid-permeable membrane associated with an adjoining filter plate, wherein at least one diaphragm is expandable toward an adjoining filter plate effective to promote solid/liquid separation in an abrasive suspension introduced into the flow passages in which liquid is transmitted through the adjoining liquid-permeable membrane; and wherein the filter plates include respective interior filtrate drainage chambers for drainage of liquid filtered from the abrasive suspension.

2. The method according to claim 1, wherein said abrasive particles are polishing agents selected from the group consisting of precipitated silica, silica gels, dicalcium phosphate, calcium pyrophosphate, and precipitated calcium carbonate.

3. The method according to claim 1, wherein the at least one diaphragm expands towards an adjoining filter plate by

TABLE V

|  | Toothpaste Formula # | | | | | | |
| --- | --- | --- | --- | --- | --- | --- | --- |
|  | 1 | 2 | 3 | 4 | 5 | 6 | 7 |
| 24 hr. Viscosity, cP | 420,000 | 590,000 | 570,000 | 620,000 | 320,000 | 310,000 | 270,000 |
| 1 Wk Viscosity, cP | 500,000 | 690,000 | 600,000 | 530,000 | 390,000 | 390,000 | 400,000 |
| 3 Wk Viscosity, cP | 600,000 | 750,000 | 700,000 | 650,000 | 440,000 | 390,000 | 440,000 |
| 25% pH | 6.65 | 6.63 | 6.63 | 6.68 | 6.8 | 7.81 | 7.55 |
| Standup | 9 | 9 | 9 | 9 | 9 | 9 | 9 |
| separation | 9 | 9 | 9 | 9 | 9 | 9 | 9 |
| RDA | — | — | — | — | 67 | 67 | 58 |
| PCR | — | — | — | — | 92 | 88 | 81 |

Toothpaste formulated with the inventive silica slurry compositions had good viscosity and aesthetic properties.

It will be understood that various changes in the details, materials, and arrangements of the parts which have been described and illustrated herein in order to explain the nature of this invention may be made by those skilled in the art without departing from the principles and scope of the invention as expressed in the following claims.

What is claimed is:

1. A method for preparing an abrasive slurry composition, comprising the steps of:

introducing, into a reactor container, reaction mixture contents comprising reactants effective to form a suspension of water-insoluble abrasive particles;

introduction of heated fluid effective to expand the diaphragm and heat the abrasive suspension effective to promote water removal.

4. The method according to claim 1, wherein the drainage chambers being connected to a vacuum source effective to remove vaporized portions of the abrasive suspension.

5. The method according to claim 1, further comprising a step of combining the abrasive composition with at least one of additional water, binder, fluoride ion-providing compound, flavoring agent, coloring agent, whitening agent, preservative, tartar control compound, foaming agent, and anti-microbial agent.

6. A method for preparing an abrasive slurry composition, comprising the steps of:

introducing, into a reactor container, reaction mixture contents comprising alkali silicate and acid with intermixing thereof to form an abrasive suspension comprising particles of precipitated silica;

partially dewatering the abrasive suspension, comprising the substeps of:

(i) feeding the abrasive suspension into a chamber filter press in which the suspension is filtered by a plurality of adjoining chamber filter plates to partially dewater the suspension to produce first filter cake material;

(ii) further dewatering the first filter cake material under reduced pressure in the interior of the chamber filter and with heating to provide second filter cake material having a solids content of 40 to 90% by weight;

fluidizing the precipitated silica particles in the second filter cake material by combining humectant with the precipitated silica particles thereof with mixing effective to provide an aqueous suspension of precipitated silica particles; and wet grinding the aqueous suspension of precipitated silica particles;

wherein the chamber filter press includes a plurality of alternating i) filter plates covered by respective liquid-permeable filter membranes, and ii) diaphragm squeeze plates that each include a diaphragm that is expandable toward an adjoining filter plate; wherein the squeeze plates and filter plates define abrasive suspension flow passages being the areas between each diaphragm included with a squeeze plate and each liquid-permeable membrane associated with an adjoining filter plate, wherein at least one diaphragm is expandable toward an adjoining filter plate effective to promote solid/liquid separation in an abrasive suspension introduced into the flow passages in which liquid is transmitted through the adjoining liquid-permeable membrane; and wherein the filter plates include respective interior filtrate drainage chambers for drainage of liquid filtered from the abrasive suspension.

7. The method according to claim 6, wherein said abrasive particles are polishing agents selected from the group consisting of precipitated silica, silica gels, dicalcium phosphate, calcium pyrophosphate, and precipitated calcium carbonate.

8. The method according to claim 6, wherein the at least one diaphragm expands towards an adjoining filter plate by introduction of heated fluid effective to expand the diaphragm and heat the abrasive suspension effective to promote water removal.

9. The method according to claim 6, wherein the drainage chambers being connected to a vacuum source effective to remove vaporized portions of the abrasive suspension.

10. The method according to claim 6, further comprising a step of combining the abrasive composition with at least one of additional Water, binder, fluoride ion-providing compound, flavoring agent, coloring agent, whitening agent, preservative, tartar control compound, foaming agent, and anti-microbial agent.

* * * * *